United States Patent
Odernheimer

[11] Patent Number: 5,216,925
[45] Date of Patent: Jun. 8, 1993

[54] APPARATUS FOR NON-INTRUSIVE CONTINUOUS AND AUTOMATIC TAKING OF SAMPLES, STORING AND SUPPLYING OF SAMPLES AND DATA FOR A POSSIBLE EVALUATION

[75] Inventor: Bernhard Odernheimer, Munster, Fed. Rep. of Germany

[73] Assignee: Bruker-Franzen Analytik GmbH, Bremen, Fed. Rep. of Germany

[21] Appl. No.: 602,327
[22] PCT Filed: May 24, 1989
[86] PCT No.: PCT/DE89/00330
 § 371 Date: Nov. 26, 1990
 § 102(e) Date: Nov. 26, 1990
[87] PCT Pub. No.: WO89/11641
 PCT Pub. Date: Nov. 30, 1989

[30] Foreign Application Priority Data
May 28, 1988 [DE] Fed. Rep. of Germany ....... 3818210

[51] Int. Cl.$^5$ .................. G01N 35/00; G01N 1/10; G01N 1/22
[52] U.S. Cl. ................ 73/863.12; 73/863.21; 73/860.91; 369/273; 422/66
[58] Field of Search .......... 73/863.12, 863.21, 864.72, 73/864.91; 346/135.1; 369/273; 422/66

[56] References Cited
U.S. PATENT DOCUMENTS
3,102,512 9/1963 Broerman ................. 73/863.12 X
4,541,268 9/1985 Odernheimer ................. 73/31.07

FOREIGN PATENT DOCUMENTS
518473 5/1979 Australia .
0055624 7/1982 European Pat. Off. .
1900808 8/1970 Fed. Rep. of Germany .
253867 12/1985 Japan ................. 73/863.12
2169078 7/1986 United Kingdom ............ 73/863.12

OTHER PUBLICATIONS
"Automatisierungs-System für Klinisch-Chemische Laboratories SILAB"; *Siemens Zeitschrift;* May 1973; p. 10 Article containing interview between Journal editor and Dr. MacKnedel.

*Primary Examiner*—Tom Noland
*Attorney, Agent, or Firm*—Walter A. Hackler

[57] ABSTRACT

The object of the invention is a method and a suitable apparatus for continuous and automatic taking of samples together with the correlating data and successive possible evaluation of the samples and data in a simple way. A storage tape (1) for samples and data is contacted with a sample storing head (2) and a data recording head (3) when storing. During readout the tape is contacted with a sample taking head (4) of an analyzing instrument (14) and a sample data reading head (5). Thus the invention makes it possible to permanently control chemical processes in production processes as well as in other creations of undesired and/or noxious liquid or gaseous chemical substances and/or compounds.

12 Claims, 3 Drawing Sheets

APPARATUS FOR NON-INTRUSIVE CONTINUOUS AND AUTOMATIC TAKING OF SAMPLES, STORING AND SUPPLYING OF SAMPLES AND DATA FOR A POSSIBLE EVALUATION

BACKGROUND OF THE INVENTION

The invention concerns a method and an apparatus for non-intrusive continuous and automatic taking of samples with material and data-like storing of the samples for long-term disposing of the samples and data for a possible evaluation according to criteria which can be defined later on.

The invention generally refers to the field of sampling and storing of samples for the analysis of gasses and liquids as well as sample input into an apparatus for analysis. The invention can for example be applied in investigating a chemical process in a chemical factory, a chemical accident or any other environmental polluting event in retrospection, e.g. the content of a reaction mixture with respect to the main components as a function of time, the contamination of the air in the environment of a depot for chemicals or river water at the places of sewage input. Besides process control and environment control the verification of the non-production of chemical weapons is a potentially important field of application. In case of suspection of a violation of a respective restriction treaty the invention offers a simple possibility of retrospective analysis of samples, which can be exactly related to relevant data like day/time of the sample storage, temperature profiles, pressures and fluxes. An effective continuous sampling and storing of samples for the reason of controlling in the fields mentioned above has not yet been practiced. Recently the lack of a simple, reliable system for sampling and sample storing has become apparent by spectacular chemical accidents.

Many instruments and apparatuses which were employed in former times for the controlling of chemo-technical processes are indeed nowadays used for controlling the environment, the purity of food and the concentration of noxious substances. These instruments for analysis sometimes work continuously but realize the analysis at once in an on-line-operation, that means they do not store samples and correlating data. In exceptional cases liquid or gaseous samples as they are or in an enriched form are applied on sorbents like Tenax or XAD and stored until analysis is performed. For this purpose there are sample collectors and auto injectors for gas chromatography on the market, the latter for the automatic input of the sorbed chemical components into an instrument for analysis, for example into a combination of a gas chromatograph and mass spectrometer.

A multiple passive probe collector with the possibility of fast input of the sample into the input head of an instrument for analysis has been described as an advantageous alternative to Tenax- and XAD-sorption tubes (DE-A 3,137,765 and U.S. Pat. 4,541,268). Here the ability of an sorptive collecting plate for sample enriching, sample storage and sample desorption after transfer to the heated input head of a mass spectrometer or any other instrument for analysis is used. As sorbent for example a silicone membrane can be used.

Moreover an automatic system for clinical-chemical laboratories called "SILAB" has been published in the periodical Siemens-Zeitschrift, No. 5 of May 1973. The field of application of "SILAB" touches the biological-chemical analyzing and evaluating of the results at the point, where so-called laboratory automats are used.

Sampling and evaluating are closely connected with respect to the time in this case. Each analysis is evaluated and it is the declared purpose to accelerate the medical diagnostics by means of mechanization and rationalization including the use of data processing (at the state of the art of 1973) and to meet the demands of an increasing number of necessary examinations. The biological substances that are to be examined are usually perishable, which means chemical-biological changing, and, therefore, must be brought to the examination in short time intervals. The durability of each sample is very limited, but because of apt vessels for the examinations (e.g. for blood and serum) a relatively large space is required.

The automatic system "SILAB" works only according to a discontinuous machining cycle which must be defined in advance for special samples, in a close time connection to a given equipment and using given evaluation criteria. The advantages lie only in rationalization and rise of the output of the required chemical-clinical laboratory works.

The techniques according to the state of the art are consumptuous with respect to the space requirements, the costs for producing and operating and with respect to the personnel requirements. Furthermore, they are hardly fully automatized and subject to disturbances. The correlation between certain relevant data associated with a sample, e.g. day, time, temperatures, pressures, flux-rates, etc. is connected with a consumptuous protocolling and therefore subject to error. Moreover, the correlation of the data can easily be manipulated. Sample analysis is often time-consuming and difficult, whereby the information of interest about the sample has to be selected out of a variety of undesired data which are either irrelevant with respect to the analytical questions or even secret.

Until now no simple automatic sampling method has been published which would be apt to detect in case of need one or more chemical components in a gas or liquid mixture subsequently and with exact correlation to relevant data of the sampling like time, temperatures, etc.

SUMMARY OF THE INVENTION

The purpose of the invention is therefore to provide a method and an apparatus for non-intrusive continuous and automatic sample taking and storing, in which besides the material storing of the samples a simultaneous acquisition and recording of the correlated data is accomplished in a space saving way, so that the samples and data can be deposited in readiness for being evaluated later on in a simple way and after criteria which are defined at this later time. The solution of the problem is accomplished by the following method and apparatus.

The method according to the invention is characterized by the following process steps:

By use of a pump (7) a sample stream (6) is created, from this sample stream (6) a sample is taken and applied to an sorpteous storage body (1) by means of a sample storing head (2) at a suitable restriction (8), the sample penetrates into the sorption layer (12) of the storage body (1) by means of solution and diffusion and forms there a sample spot (9) or a sample trace (9), simultaneously with the sample storing the correlating data are recorded on the storage body (1) in a data track (11) by means of a data recording head (3), for the evaluation of the sample the storage body (1) is brought into contact with a sample taking head (4) by means of a contact membrane (13) or a contact tissue (13), the sample is partly or fully desorbed out of the sample spot (9) of the sorption layer of the storage body (1) by the influence of temperature, the sample is transported to the analyzer (14) by means of a carrier gas stream (15), the correlating data are read out of the data track (11) by means of a data reading head (5).

Further the sample storage rate can be controlled by the thickness of the walls and the temperature of a silicone rubber functioning as a restriction and optimized according to the substance.

The apparatus for performing the method according to the invention is comprised of the following components in accordance with claim 1:

A means for continuous and automatic sample taking and storing of samples and recording of the correlating data, comprised of an sorptive storage body (1) which is either magnetizable or can be optically labeled, a sample storing head (2) and a data recording head (3), a means for material and data-like evaluation of samples, comprised of a storage body (1) with the samples and data, a sample taking head (4) and a data reading head (5).

Claim 2 suggests a multilayer construction for the storage body comprised of the following layers:

a sorption layer (12) for the storage of the samples, a magnetizable layer (20) or a layer which can be labelled optically for the recording of the correlating data, preferably an additional layer (21) as a diffusion barrier against adjacent stored samples.

In claim 7 the arrangement of the means for continuous and automatic sample taking and storing comprised of a sample storing head, a pump, a restriction and a heating block is shown.

Claim 9 shows the components of the means for material evaluation of the samples, comprised of a sample taking head which is comprised of a heating block, a contact membrane or a contact tissue and an instrument for analysis following thereafter.

According to claim 8 the restriction consists of silicone rubber.

The other dependent claims specify additional and/or alternative features of the inventive apparatus.

The principle of the solution according to the invention is based besides others on the fact, that the samples can be materially stored on a common storage body which can be multilayered and the correlating data can be recorded at the same storage body, e.g. magnetically or optically. Moreover, the invention comprises the means for storing the samples and recording the accompanying data as well as the means for evaluating the stored samples and the recorded data.

By the present invention a reliable storage of samples in an appropriate amount (according to the dimensioning and capacity of the sample storage tape) and the automatic association of relevant data (e.g. day/time of the sample storing) and in case of need the quick input of samples is accomplished in a simple way. The apparatus can be constructed like a magnetic tape cassette in a space saving way and can be made difficult to manipulate by total encapsulating. The coupling of the data carrier and the sample carrier guarantees the quick finding of a certain sample and makes any bookkeeping about data concerning the samples unnecessary.

The present invention gives the possibility of non-intrusive, i.e. not distrubing, but continuous sample taking together with the storage of the identifying data. A later evaluation of the stored sample and data independent of time and place is accomplished by the mobile use and storage of the storage cassettes. A great number of samples can be stored for a long time and protected against chemical influences and against unauthorized evaluation (data protection). Such a method and an apparatus especially adapted for this method accomplishes a control of chemical production in bigger as well as in smaller companies.

In contrast to the above mentioned automatic system "SILAB" the field of application of the present invention lays generally in the (non-biological) chemistry and there especially in the production of chemicals, especially those which can be weaponized as chemical weapons. Moreover a plurality of samples, especially diffusible substances (liquids and gasses) are to be stored for a long term in a small space and are to be protected against outer influences, i.e. against chemical changes. These samples can usually be found only in trace concentrations, i.e. in the region of micro samples. The present non-intrusive method is to avoid distrubing and impeding interferences with the production of chemical products, but nevertheless to take continuously samples after predefined time intervals and to store them materially as well as to identify them data-like.

In a special means for continuous sample taking and storing of samples and their correlating data according to the claims 2 to 6, generally comprised of a storage body in a storage cassette a variety of samples and informations can be stored in a relatively small space.

With the method according to the present invention and the according specifically developed apparatus an analysis which eventually becomes necessary at a later time can be performed after predefined time intervals of continuous sample taking independent of the actual time and the equipment and after criteria which can be defined at any time. This system makes the evaluation of the samples possible but does not necessitate the evaluation.

A subsequent exact inspection of an incident or an event for which the detection of a chemical or noxious substance is of importance, i.e. the subsequent detection of an illegal or unintended production of dangerous and/or prohibited substances can be realized by the invention.

Thus the invention allows a probative documentation about the sequence of chemical processes or the presence of certain chemical substances at certain times during a production process, but also in the sewage air and sewage water of certain factories, in the sewage of garbage depots and so on. The invention is especially adapted to control or at least to detect the production of chemical weapons in the context of national or international treaties.

The invention can be e.g. of importance for the on-site inspection in connection with the verification of a Convention banning chemical weapons. Discussions about the possibilities of verification of non-production of chemical weapons make it apparent, that there exists a special need in this field. Especially problematic is the in-loco controlling of industrial plants, where industrial secrets have to be protected, but the necessary data for the controlling have yet to be accessible in an appropriate amount and quality. Furthermore the invention can be of use in the controlled destruction of existing chemical weapons stock piles, in the controlled production of chemical weapons in an allowed small amount for research reasons, or in the verification of the use of chemical weapons infringing international law in military conflicts.

BRIEF DESCRIPTION OF THE DRAWINGS

In the following, embodiments of the invention are described in detail with reference to drawings.

DETAILED DESCRIPTION OF THE INVENTION

Figure 1A:
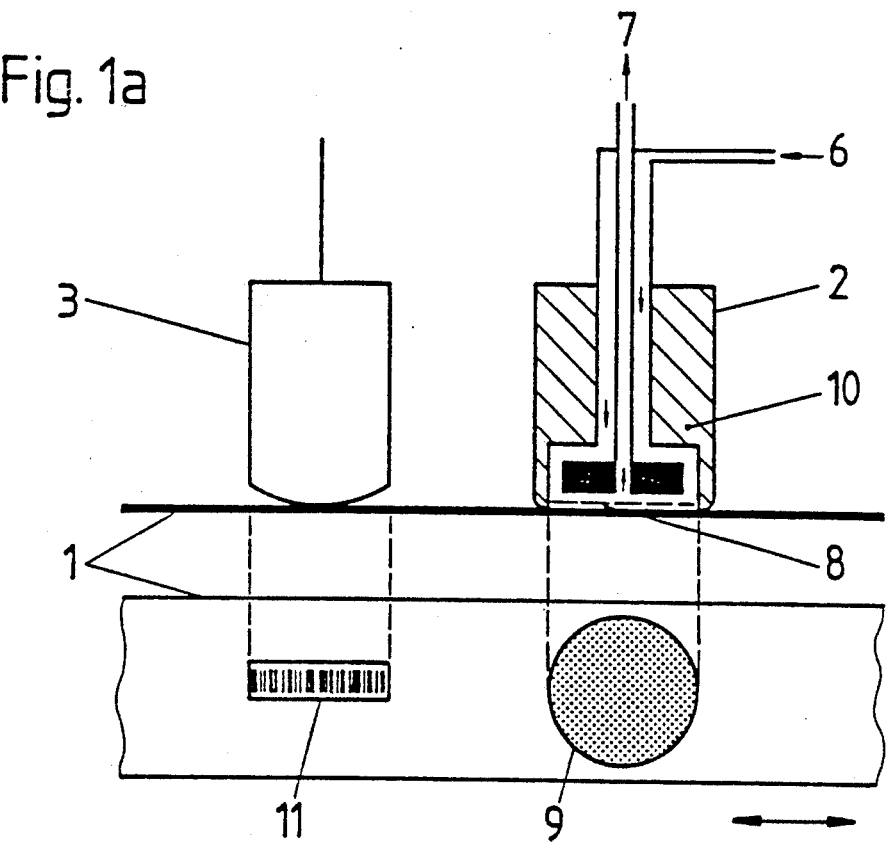
FIG. 1a shows a sectional view of the means for sample taking, sample storing and data recording as well as a view of the storage body from above.

The storage of samples and correlating data according to the invention is shown in FIG. 1a. A storage body 1, shown as a storage tape, for samples and data is in contact with the sample storing head 2 and the data recording head 3 during the storing process.

Figure 1B:
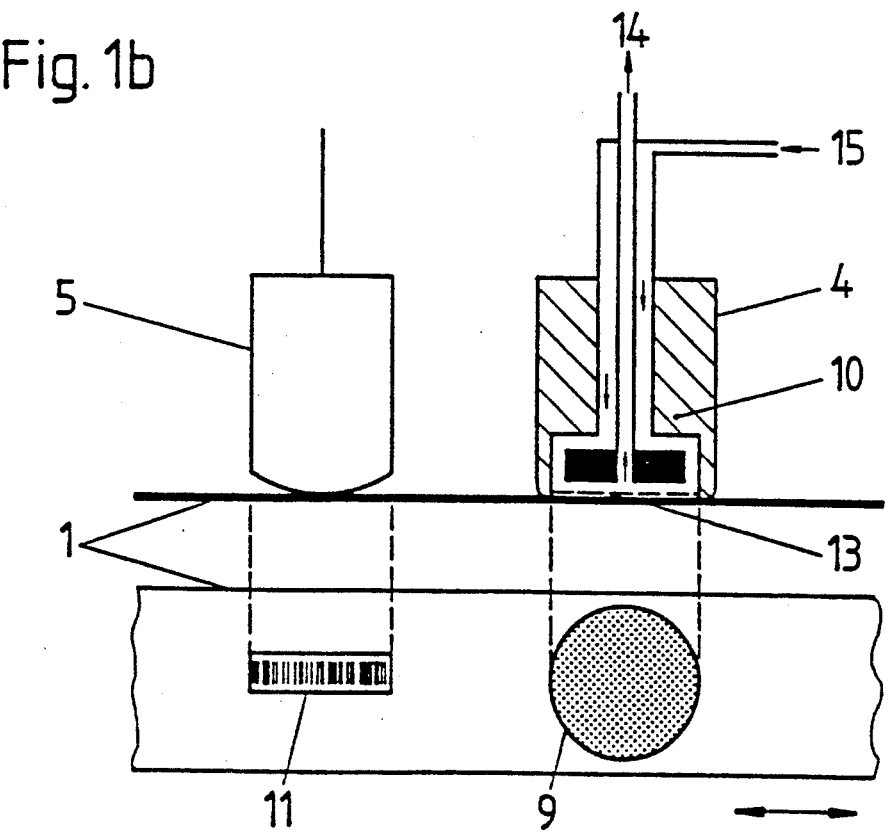
FIG. 1b shows a sectional view of the means for the material and data-like evaluation of the samples and a view of the storage body from above.

FIG. 1b shows the read-out of the samples and data, storage body 1 being in contact with sample taking head 4 of an analyzing instrument 14 and the data reading head 5.

The sample storing is accomplished in the way that a sample stream 6 being a liquid or a gas is brought into contact with the sorption layer 12 of the storage body 1 having suitable wall thickness and temperature by means of a pump 7 (not shown) via a suitable restriction 8. Thus the components of the sample stream 6 are carried by solution and diffusion into the sorption layer 12 and form at the place which was exposed to the sample stream 6 a sample spot 9 or a sample trace 9. The inherent quantity of substance can be varied by the kind of restriction 8, temperature of the heating block 10, the sorption capacity of the storage tape, the time of influence of the sample stream 6 and the area of the storage tape exposed to the sample stream 6. A silicone membrane of a certain thickness (usually less than 200 $\mu$m) which is selectively permeative because of the different solubility and diffusibility especially of organic noxious substances features an especially advantageous restriction. The thickness of its layers or wall also influences the sample storage rate and the stored amount of substance. A very effective restriction is necessary if with the sample stream 6 having a flux rate of e.g. some g/min (grams per minute) taken out of a chemical reaction mixture, representative samples are to be stored in rates of the order of only some hundred ng/h (nanograms per hour).

The restriction can be totally omitted, if the sample stream 6 consists e.g. of water, especially if drinking water, sewage water or river water is to be controlled with respect to traces of dissolved organic noxious substances. In this case the sorption layer 12 of the storage tape is exposed directly to the aqueous sample stream.

The data storage in the shown embodiment of the invention is accomplished in a way known from magnetic tape storage instruments and leads to a data track 11 in a magnetizable layer 20 of the storage tape 1. In a different embodiment the data storage can be accomplished optically readable on an adapted layer, e.g. by a printer, a pen recorder, or by means of a laser beam. The drawing of the data track 11 presented here is to be understood as being schematic, i.e. the bar-code pattern shown is not a necessary feature of the data track 11. However, the data tracks 11 shown in FIGS. 2a-2c may really represent a bar code pattern written by a printer or a laser beam.

The evaluation of the storage tape 1, i.e. the read-out of the samples and data, is accomplished according to the invention conversely to the storage process by bringing the sample storing sorption layer 12 is contact with the contact membrane 13 or the contact tissue 13 of the heated sample taking head 4 of an analyzing instrument 14 choosing that part of the storage tape 1 which carries the sample being associated to certain additionally stored data (time/day, temperature). During this contact the sample is desorbed thermically out of the storage tape 1 and transported by means of the carrier gas stream 15 in a gaseous form to the analyzing instrument 14 (not shown in the figure) which is preferably a gas chromatograph (GC), a mass spectrometer (MS) or a mobile GC/MS-combination, similar to the tracing system MM1 (Bruker-Franzen-Analytik) for identification and quantification of substances.

The data correlated to the samples are read out and displayed from the data track 11 in the usual way by a data reading head 5.

As shown in FIGS. 2a-d the sample storage can be accomplished continuously (or even discontinuously) and correlated with the data storing in different ways.

Figure 2A:
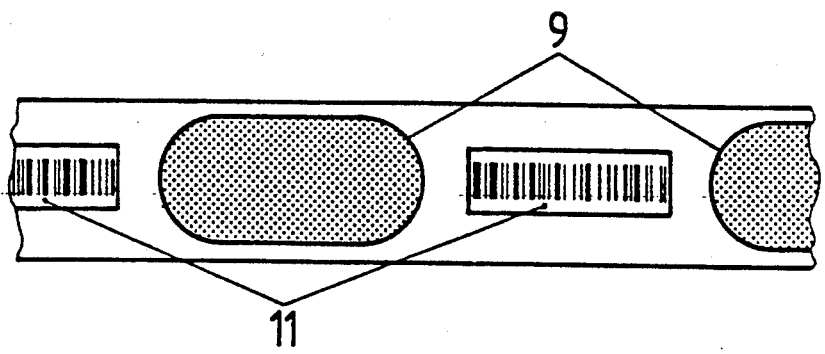
FIGS. 2a-2c show several versions of the arrangement of sample storage and data recording on the storage body.
Figure 2B:
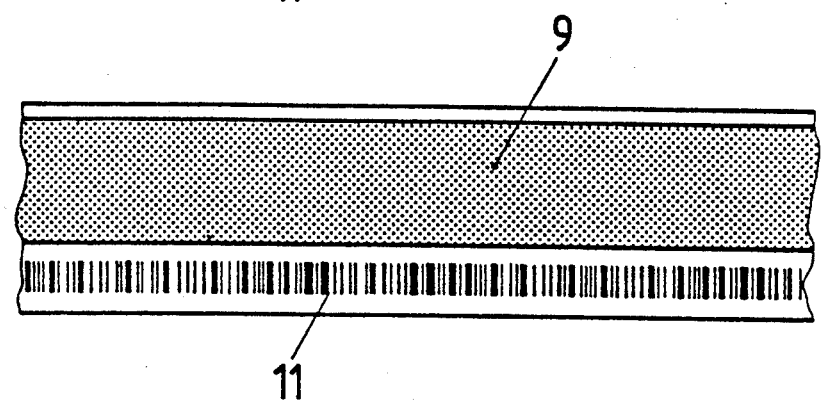

FIG. 2a shows the schematic disposition of a sample spot 9 and the data track 11 in intermittently occupied sections in the same storage tape 1 whereas the storage process is accomplished in batches, i.e. discontinuously. FIG. 2b shows a storage tape with sample trace 9 and data track 11 in adjacent arrangement.

Figure 2C:
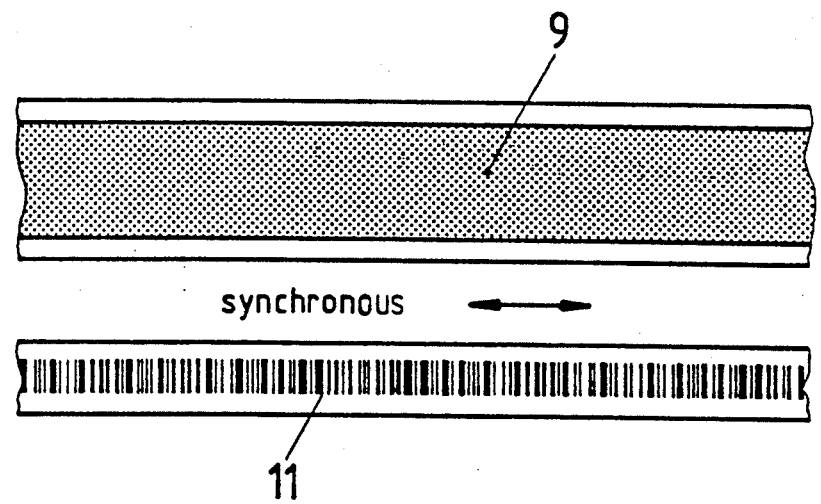

FIG. 2c shows separated storage tapes for the sample storing and data storing making possible the spatial separation of the sample storing head 2 and the data recording head 3 during the storage process as well as the use of known devices like magnetic storage devices, bar-code printers and so on. The synchronization of the tape transport mechanisms for the sample and data storage is guaranteed by means of electronic control.

Figure 2D:
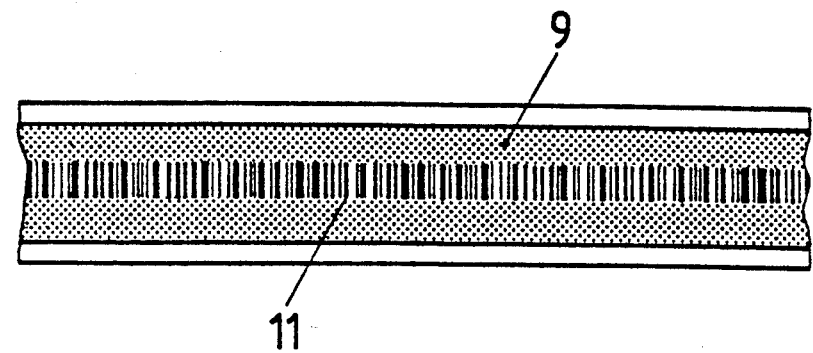
Figure 4:
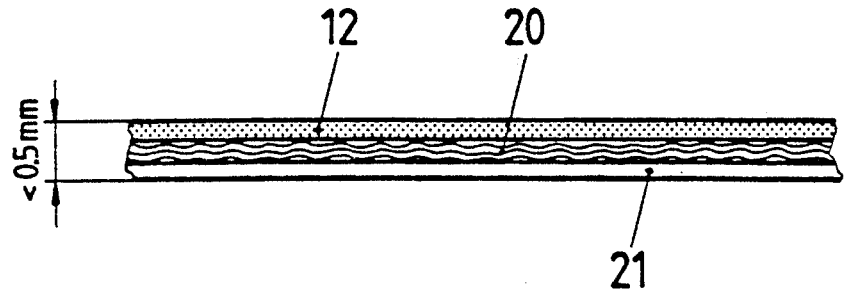
FIG. 4 shows a sectional view of one possible example of a 3-layered construction of the storage body.

FIG. 2d shows a storage tape on which samples and data are continuously stored one upon another on the same tape. For this embodiment the use of the magnetizable layer 20 shown in FIG. 4 is especially adapted.

Principally a storage disc can be used for the storage of samples and correlating data as well. The use of a storage tape is however technically easier and features a higher capacity.

Figure 3:
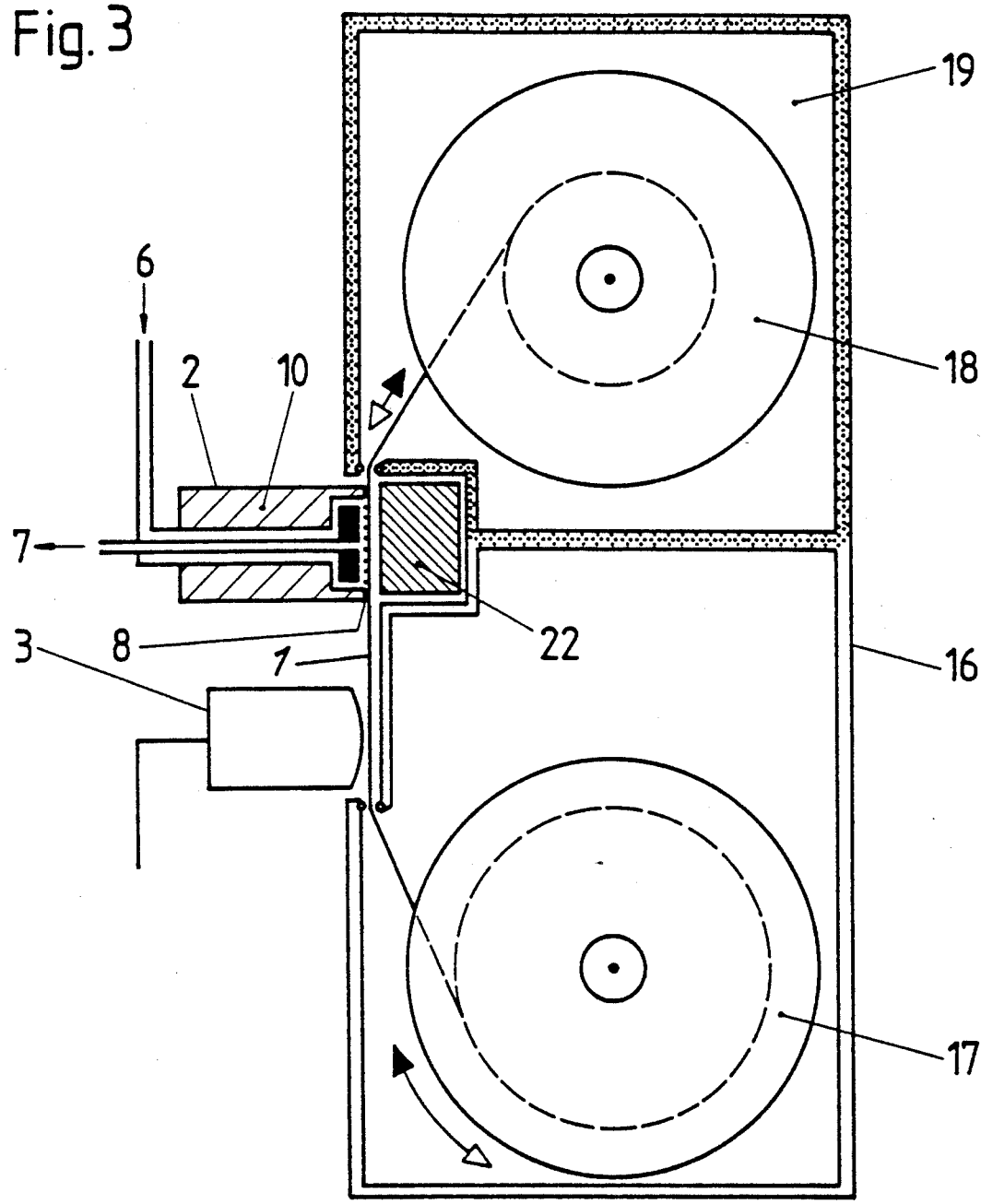
FIG. 3 shows a sectional view across a closed storage cassette comprising the means for sample taking, sample storage, data recording and a tape which can be wound around a hub and which is used as the storage body.

FIG. 3 shows schematically the storage process using a closed storage cassette 16 coupled to the sample storing head 2 and the data recording head 3 for which one of the storage modes according to FIGS. 2a, 2b or 2d is chosen.

A driving mechanism (not shown in the figures) moves the storage tape 1 which is wound from the supply hub 17 in a controlled way along the data recording head 3 and the sample storing head 2 with the thermostat block 22 to the storage hub 18 to which the storage tape 1 is wound up. The storage hub 18 is located in the chamber 19 which is held suitably on low temperature in order to keep the losses due to evaporating and decaying of the samples during long-term storage small.

FIG. 4 shows a sectional view of the storage body 1 which is shown here as a storage tape 1. The storage tape 1 in this case is comprised of three layers: The sorption layer 12 for the sample storing, the magnetizable layer 20 for the data storing and a metal layer 21 which can be formed by aluminum foil.

The latter works as a diffusion barrier and prevents the stored samples from being dispersed through adjacent windings of the storage hub or coil 18.

Instead of the reusable magnetizable layer 20 in an embodiment of the invention, a flexible plastic layer which is not shown in the figures can be used for the storage of the correlating data, the layer being coated with pigments and/or polymers. In this plastic layer, data can be written on the tape optically by means of a laser beam for example. In other embodiments of the invention for writing of the data, also printers, pen-writers etc. can be used. Especially suitable is the use of a bar-code pattern.

Since a plastic layer (foil) can be lattered only once, the safety of the data against undesired extermination or falsification is even higher. In order to gain a similar safety of the data on the data track 11 when a magnetizable layer 20 is used in an embodiment of the invention the walls of the storage tape cassette 16 are constructed as magnetic shielding. As wall material one-or multilayered soft iron, $\mu$-metal etc. can be used.

I claim:

1. Apparatus for the data-like storing of samples comprising:
    sorptive storage body means for sorbing a sample and recording of correlating data;
    means for continuous and automatic sample taking;
    sample storing head means for heating the sorptive storage body means and causing the sample to penetrate the sorptive storage body means;
    data recording head means for recording of the correlating data on said sorptive storage body means; and
    means for material and data-like evaluation of samples, penetrated into the sorptive storage body means and correlating data, comprising a sample taking head and a data reading head.

2. Apparatus according to claim 1 wherein the storage body means comprises a plurality of layers, said plurality of layers including sorption layer means for the storage of the samples, recording layer means for the recording of the correlating data, said recording layer comprising a material selected from the group consisting of a magnetizable medium and an optically labelable medium, and layer means for acting as a diffusion barrier against adjacent stored samples.

3. Apparatus according to claim 2 wherein said recording layer comprises a magnetizable medium with a data track is part of a magnetizable layer thereon.

4. Apparatus according to claim 3 further comprising storage tape cassette means for at least partially covering the magnetizable medium, said storage tape cassette having a wall material comprising a magnetic shielding material.

5. Apparatus according to claim 4 wherein the wall material of the storage tape cassette has at least one layer comprising at least one material selected from the group consisting of soft iron and $\mu$-metal.

6. Apparatus according to claim 2 wherein said recording layer comprises an optically labelable medium with a data track thereon, said optically labelable medium comprising a flexible plastic foil coated with a material selected from a group consisting of pigments and polymers.

7. Apparatus according to claim 1 wherein the sample storing head means comprises a restriction and a heating block.

8. Apparatus according to claim 7 wherein the restriction comprises silicone rubber.

9. Apparatus according to claim 1 wherein the sample taking head comprises a heating block, a member comprising a material selected from a group consisting of a contact membrane and a contact tissue, and instrument means for analysis of samples and recorded correlating data.

10. Apparatus according to claim 1 wherein the sample storage head means comprises restriction means for controlling sample storage rate on the sorption charge body means.

11. Apparatus according to claim 1, wherein said sorptive storage body means is magnetizable.

12. Apparatus according to claim 1, wherein said sorptive storage body means is optically labeled.

* * * * *